United States Patent [19]

Larkins et al.

[11] Patent Number: 4,471,136
[45] Date of Patent: Sep. 11, 1984

[54] PREPARATION OF ETHYL ACETATE

[75] Inventors: Thomas H. Larkins; Brent A. Tennant, both of Kingsport, Tenn.

[73] Assignee: Eastman Kodak Company, Rochester, N.Y.

[21] Appl. No.: 369,857

[22] Filed: Apr. 19, 1982

Related U.S. Application Data

[63] Continuation-in-part of Ser. No. 244,572, Mar. 17, 1981, abandoned.

[51] Int. Cl.³ .................... C07C 67/00; C07C 67/297; C07C 69/14
[52] U.S. Cl. .................... 560/265; 560/263; 562/607

[58] Field of Search .......................... 560/265

[56] References Cited

U.S. PATENT DOCUMENTS 4,221,918  9/1980  Suzuki ............................... 560/263

Primary Examiner—Vivian Garner
Attorney, Agent, or Firm—David E. Cotey; Daniel B. Reece, III

[57] ABSTRACT

The present invention provides a process for the preparation of ethyl acetate by hydrogenating acetic anhydride, or mixtures of acetic anhydride and ethylidene diacetate, in the presence of a Raney nickel catalyst and an organic sulfonic acid to produce ethyl acetate.

13 Claims, No Drawings

PREPARATION OF ETHYL ACETATE

DESCRIPTION

This application is a continuation-in-part of co-pending U.S. application Ser. No. 244,572, filed Mar. 17, 1981, now abandoned.

BACKGROUND OF THE INVENTION

This invention relates to a novel process for the preparation of ethyl acetate by hydrogenating acetic anhydride or mixtures of acetic anhydride and ethylidene diacetate to obtain ethyl acetate.

An economically advantageous process for the preparation of acetic anhydride by the carbonylation of methyl acetate has been reported in the patent literature. See, for example, Belgian Pat. No. 819,455, British Published Patent Application No. 2,013,184, Japanese Published Patent Applications Nos. 75-47921 and 75-47922, and U.S. Pat. Nos. 3,927,078 and 4,046,807.

Not only is acetic anhydride itself an important chemical (for example, as an acetylating agent in the manufacture of cellulose acetate and other esters), but it can be converted to ethyl acetate, which presently is derived primarily from petroleum or natural gas.

In the rhodium-catalyzed carbonylation of methyl acetate to acetic anhydride which is described in the literature, it has been found that the inclusion of about 5% hydrogen in the carbon monoxide feed gas not only suppresses tar formation but increases the reaction rate. However, the use of hydrogen results in the co-production of ethylidene diacetate. Although the amount of ethylidene diacetate is quite small compared to the anhydride produced, the total amount produced in a commercial scale operation is substantial. In the product recovery portion of an acetic anhydride plant, the ethylidene diacetate can most economically be recovered as a mixture with acetic anhydride wherein the ethylidene diacetate:anhydride weight ratio can vary from 1:4 to 4:1. To recover the carbonyl values represented by the ethylidene diacetate, it must be converted to other products. One of the most economical means for accomplishing this would be to hydrogenate the mixture to obtain acetic acid and ethyl acetate, the latter being a valuable solvent.

The hydrogenation of acetic anhydride alone using a nickel catalyst in the presence of a strong acid, e.g., HCl, HF, sulfuric acid, phosphoric acid, methanesulfonic acid, or p-toluenesulfonic acid, is disclosed in U.S. Pat. No. 4,221,918. However, the products obtained are reported to be ethylidene diacetate, acetic acid, and, when HCl was the acid used, 1-chloroethyl acetate.

Acetic anhydride by itself can be hydrogenated to ethyl acetate and acetic acid using only a Raney nickel catalyst (see co-pending and commonly assigned U.S. application Ser. No. 244,578, filed Mar. 17, 1981). However, it has been found that relatively severe reaction conditions are required when only Raney nickel is used. Furthermore, in mixtures of acetic anhydride and ethylidene diacetate, e.g., 50:50 weight mixtures, not only does ethylidene diacetate appear to resist hydrogenation but it also appears to retard the hydrogenation of the acetic anhydride present.

Thus, there existed a need for a commercial process capable of converting acetic anhydride and mixtures thereof with ethylidene diacetate to ethyl acetate.

We have discovered that milder conditions can be employed in hydrogenating acetic anhydride or mixtures of acetic anhydride and ethylidene diacetate in the presence of Raney nickel if an organic sulfonic acid is present during the hydrogenation. Not only does the presence of the organic sulfonic acid permit the use of milder and thus more economical operating conditions but its use results in significantly greater overall conversions.

SUMMARY OF THE INVENTION

The present invention provides a process for the preparation of ethyl acetate. The process comprises hydrogenating acetic anhydride or a mixture thereof with ethylidene diacetate at elevated pressure and temperature in the presence of a catalytic amount of a catalyst system comprising Raney nickel and an organic sulfonic acid.

DETAILED DESCRIPTION OF THE INVENTION

The process of the present invention comprises hydrogenating acetic anhydride or a mixture thereof with ethylidene diacetate at elevated pressure and temperature in the presence of Raney nickel and an organic sulfonic acid. The feed to the hydrogenation reactor can, if desired, contain an inert solvent such as acetic acid in addition to acetic anhydride and ethylidene diacetate, if present. The co-product acetic acid may be converted to methyl acetate and used in the production of acetic anhydride.

The concentration of the Raney nickel in the present process can be varied substantially depending on such factors as the temperature and pressure employed, the product and/or space-time yield desired, the capability to dissipate the heat of reaction, etc. Generally, concentrations in the range of about 0.1 to 10 weight percent, based on the total weight of acetic anhydride and ethylidene diacetate, if any, will give good results when using appropriate pressures and temperatures. Raney nickel concentrations (same basis) of about 0.5 to 2.5 weight percent will most often be used.

The amount of organic sulfonic acid used also can be varied significantly depending, for example, on the particular acid used and those factors set forth above with respect to the amount of Raney nickel used. The amount of organic sulfonic acid used may range from about 0.1 to 3.0 weight percent based on the total weight of the acetic anhydride and ethylidene diacetate, if any, charged to the hydrogenation reactor. The preferred range is about 0.5 to 1.5 weight percent. Of the many organic sulfonic acids that may be used in the process, methanesulfonic acid, p-toluenesulfonic acid, and mixtures thereof are preferred because of their cost.

The temperature at which the process of this invention may be carried out should be in the range of about 100° to 250° C. However, it is preferred to operate at a temperature of about 130° to 180° C., and most preferably at about 140° to 160° C. Temperatures much below 130° C. result in poor overall conversion of the acetic anhydride and, especially, the ethylidene diacetate. The use of temperatures significantly above 180° C. will result in decomposition of not only the ethyl acetate but of some of the coproduct acetic acid.

Pressure has been found not to be nearly as important as temperature. Pressures (total reaction pressure) in the range of about 3,000 to 35,000 kPa (500 to 5000 psig) are suitable. Preferably, pressures of 3,000 to 20,000 kPa (about 500 to 3000 psig) may be used, although the use of pressures in excess of 10,000 kPa (about 1500 psig) normally is not advantageous. Pressures of 3,000 to 10,000 kPa are most preferred.

The process of the invention may be carried out as a batch operation or, more suitably, as a continuous process wherein acetic anhydride and ethylidene diacetate, if present, are continuously fed to an autoclave-like reactor and the reaction mixture containing the desired products is continuously removed, for example, as a liquid using a filter leg or as a vapor. Unreacted materials and co-product acetic acid may be removed from the reactor take-off, for example, in a distillation train, and recycled to the reactor. Any acetaldehyde that is present in the product stream may be removed by contacting it with acetic anhydride and a small amount of an organic sulfonic acid in a product separation column, e.g., in a countercurrent mode. The two compounds will react to form ethylidene diacetate which, along with the other unreacted materials, can be taken as the underflow from the column and returned to the reactor.

The process of the invention is further illustrated by the following Examples.

EXAMPLES 1-17

A mixture of acetic anhydride (50 g) and ethylidene diacetate (50 g) was hydrogenated in the presence of varying amounts of Raney nickel (Examples 1-9) and Raney nickel promoted with p-toluenesulfonic acid (Examples 10-17) using different temperatures and total autoclave pressures W. R. Grace Raney nickel No. 28 was used in all of these Examples. The acetic anhydride, ethylidene diacetate, Raney nickel catalyst, and p-toluenesulfonic acid (when used) were loaded into a 300 ml Hastelloy B autoclave designed to operate in a rocking mode. The autoclave was purged with about 700 kPa (about 100 psig) hydrogen gas pressure at room temperature and then the gas was vented. The autoclave internal pressure was increased to about 70 kPa (about 10 psig) by adding hydrogen gas at room temperature. The autoclave was sealed and heated and rocked until reaction temperature was reached, at which time additional hydrogen gas was added to increase the autoclave internal pressure to the predetermined value. The time at which the autoclave internal pressure reached the predetermined value was taken as the start of the reaction time. The reaction time used was 2 hours in Examples 1-9 and 1 hour in Examples 10-17. Reactor pressure was maintained at the preset value during the experiment by adding hydrogen gas at the same rate at which it was consumed by the reactants. When the predetermined reaction time was completed the autoclave was cooled by a stream of cold air. After the gas was vented from the autoclave the reaction product was analyzed by gas chromatographic methods.

Table 1 shows the temperature (°C.) and pressure (psig) used, the amount of nickel catalyst (Cat., g) and p-toluenesulfonic acid (PTSA, g) charged, the amount (in moles) of ethyl acetate (EA) produced, the percent of acetic anhydride (Ac$_2$O) and ethylidene diacetate (EDA) consumed (cons.) and the product yield (PY, percent of theory) and space-time yields (STY, in grams/liter liquid-hour) for ethyl acetate.

TABLE I

| Ex. | Cat. | PTSA | Temp. (°C.) | Press. (psig) | EA | Ac$_2$O Cons. | EDA Cons. | EA PY | EA STY |
|---|---|---|---|---|---|---|---|---|---|
| 1 | 1.5 | — | 190 | 1500 | .20 | 77.6 | 32.4 | 66.6 | 88 |
| 2 | 2.5 | — | 170 | 750 | .20 | 91.8 | 11.3 | 75.4 | 88 |
| 3 | 0.5 | — | 210 | 750 | .13 | 36.7 | 55.9 | 46.4 | 57 |
| 4 | 0.5 | — | 170 | 2250 | .12 | 46.9 | 8.8 | 82.7 | 53 |
| 5 | 2.5 | — | 210 | 750 | .21 | 67.4 | 76.5 | 49.4 | 92 |
| 6 | 2.5 | — | 170 | 2250 | .25 | 100.0 | 17.6 | 82.0 | 110 |
| 7 | 0.5 | — | 210 | 2250 | .43 | 98.0 | 79.4 | 84.3 | 189 |
| 8 | 2.5 | — | 210 | 2250 | .43 | 100.0 | 85.3 | 80.4 | 189 |
| 9 | 0.5 | — | 170 | 750 | .09 | 26.5 | 50.0 | 38.4 | 40 |
| 10 | 2.0 | 1.5 | 110 | 1000 | .08 | 58.2 | 2.4 | 52.5 | 70 |
| 11 | 2.0 | 0.5 | 110 | 2000 | .11 | 81.6 | 7.1 | 49.1 | 97 |
| 12 | 2.0 | 0.5 | 150 | 1000 | .31 | 99.6 | 63.8 | 67.1 | 273 |
| 13 | 2.0 | 1.5 | 110 | 2000 | .10 | 69.4 | 0.3 | 55.6 | 84 |
| 14 | 2.0 | 1.5 | 150 | 1000 | .39 | 99.8 | 97.4 | 67.0 | 345 |
| 15 | 2.0 | 0.5 | 150 | 2000 | .28 | 100.0 | 93.5 | 49.7 | 246 |
| 16 | 2.0 | 1.5 | 150 | 2000 | .43 | 100.0 | 100.0 | 74.2 | 382 |
| 17 | 2.0 | 0.5 | 110 | 1000 | .09 | 62.9 | 3.5 | 51.8 | 76 |

Table I illustrates the advantages which result from the use of the organic sulfonic acid. In Example 14, almost all of the ethylidene diacetate was consumed, whereas in Example 6, using significantly more severe conditions but in the absence of an organic sulfonic acid, only 17.6% of the ethylidene diacetate was consumed. It should be noted that each of Examples 1-9 employed more severe reaction conditions and longer reaction times than were employed in Examples 10-17, yet the results of Examples 1-9 are no better, and in many cases much poorer, than those reported for Examples 10-17.

EXAMPLES 18-21

Acetic anhydride (100 g) was hydrogenated for 60 minutes at varying temperatures and about 14,000 kPa (2000 psig) total pressure in the presence of 2 g of Raney nickel No. 28 and 0.5 g of p-toluenesulfonic acid. The operating and analytical procedures used for each Example were the same as described above for Examples 1-17. Table II shows the temperature (°C.) used, the amounts (in moles) of acetic acid (HOAc), acetic anhydride (Ac$_2$O), ethylidene diacetate (EDA), and ethyl acetate (EA) found in the reaction product and the product yield (% of theory) for ethylidene diacetate and ethyl acetate.

TABLE II

| Ex. | Temp. (°C.) | HOAc | Ac$_2$O | EDA | EA | EDA PY | EA PY |
|---|---|---|---|---|---|---|---|
| 18 | 100 | .41 | .59 | .06 | .07 | 31 | 35 |
| 19 | 120 | .68 | .28 | .11 | .14 | 31 | 41 |
| 20 | 150 | 1.18 | .01 | .02 | .30 | 4 | 61 |
| 21 | 180 | 1.25 | — | — | .30 | 0 | 61 |

It can be seen from the data provided in Table II that the process of the present invention provides excellent selectivity for ethyl acetate, especially at the preferred temperatures in the range of about 130°–180° C. In each example, ethyl acetate was a major product, with little or no ethylidene diacetate being observed in the product mixture at preferred temperatures.

COMPARATIVE EXAMPLES 1–4

Examples 18–21 were repeated except that the Raney nickel catalyst component was replaced with 1.0 g of 5% palladium-on-carbon catalyst. Table III shows, as described above, the results obtained.

TABLE III

| Comp. Ex. | Temp. (°C.) | HOAc | Ac₂O | EDA | EA | EDA PY | EA PY |
|---|---|---|---|---|---|---|---|
| 1 | 100 | .39 | .29 | .31 | 0 | 90 | 0 |
| 2 | 120 | .56 | .01 | .43 | .003 | 88 | 0 |
| 3 | 150 | .79 | 0 | .21 | .06 | 43 | 12 |
| 4 | 180 | 1.01 | .01 | .01 | .116 | 2 | 24 |

The results given in Table III illustrate the advantages provided by the process of the present invention. Prior art processes which utilized the combination of palladium-on-carbon and organic sulfonic acid catalyst components, as represented by the present Comparative Examples, yielded a product mixture which included ethylidene diacetate as a major component, with ethyl acetate being observed in moderate quantities only at temperatures of at least 180° C. In contrast, the process of the present invention, which utilizes a combination of Raney nickel and organic sulfonic acid catalyst components, requires less severe reaction conditions, as illustrated by the preceding Examples.

Although the invention has been described in considerable detail with particular reference to certain preferred embodiments thereof, variations and modifications can be effected within the spirit and scope of the invention.

We claim:

1. A process for the preparation of ethyl acetate which comprises hydrogenating acetic anhydride or a mixture thereof with ethylidene diacetate at a pressure of about 3000 to 35000 kPa and a temperature of about 100° to 250° C. in the presence of a catalytic amount of a catalyst system comprising Raney nickel and an organic sulfonic acid.

2. The process of claim 1 wherein the Raney nickel catalyst component is present in a concentration of about 0.1 to 10 weight percent, based upon the total weight of the acetic anhydride and, if present, ethylidene diacetate.

3. The process of claim 1 wherein the organic sulfonic acid catalyst component is present in a concentration of about 0.1 to 3 weight percent, based upon the total weight of the acetic anhydride and, if present, ethylidene diacetate.

4. The process of claim 1 wherein the organic sulfonic acid catalyst component comprises methanesulfonic acid, p-toluenesulfonic acid, or a mixture thereof.

5. A process for the preparation of ethyl acetate which comprises hydrogenating a mixture of acetic anhydride and ethylidene diacetate at a pressure of about 3000 to 35000 kPa and a temperature of about 100° to 250° C. in the presence of a catalyst system comprising Raney nickel and an organic sulfonic acid.

6. The process of claim 5 wherein the hydrogenation is conducted at a pressure of about 3,000 to 20,000 kPa and a temperature of about 130° to 180° C.

7. The process of claim 5 wherein the Raney nickel catalyst component is present in a concentration of about 0.1 to 10 weight percent, based upon the total weight of acetic anhydride and ethylidene diacetate.

8. The process of claim 5 wherein the organic sulfonic acid catalyst component is present in a concentration of about 0.1 to 3 weight percent, based upon the total weight of acetic anhydride and ethylidene diacetate.

9. The process of claim 5 wherein the organic sulfonic acid comprises methanesulfonic acid, p-toluenesulfonic acid, or a mixture thereof.

10. A process for the preparation of ethyl acetate which comprises hydrogenating a mixture of acetic anhydride and ethylidene diacetate at a pressure of 3,000 to 20,000 kPa and a temperature of 130° to 180° C. in the presence of a catalyst system comprising 0.1 to 10 weight percent of Raney nickel and 0.1 to 3 weight percent of an organic sulfonic acid selected from methanesulfonic acid, p-toluenesulfonic acid, or a mixture thereof, the weight percentages being based upon the total weight of acetic anhydride and ethylidene diacetate.

11. The process of claim 10 wherein the hydrogenation is conducted at a pressure of about 3,000 to 10,000 kPa and a temperature of about 140° to 160° C.

12. The process of claim 10 wherein the Raney nickel catalyst component is present in a concentration of about 0.5 to 2.5 weight percent, based upon the total weight of acetic anhydride and ethylidene diacetate.

13. The process of claim 10 wherein the organic sulfonic acid catalyst component is present in a concentration of about 0.5 to 1.5 weight percent, based upon the total weight of acetic anhydride and ethylidene diacetate.

* * * * *